(12) United States Patent
Hayes et al.

(10) Patent No.: US 9,839,441 B2
(45) Date of Patent: Dec. 12, 2017

(54) SURGICAL TOOL ARRANGEMENT AND SURGICAL CUTTING ACCESSORY FOR USE THEREWITH

(71) Applicants: James M. Hayes, San Jose, CA (US); Brian Fouts, San Martin, CA (US)

(72) Inventors: James M. Hayes, San Jose, CA (US); Brian Fouts, San Martin, CA (US)

(73) Assignee: Stryker Corporation, Kalamazoo, MI (US)

( * ) Notice: Subject to any disclaimer, the term of this patent is extended or adjusted under 35 U.S.C. 154(b) by 386 days.

(21) Appl. No.: 14/188,995

(22) Filed: Feb. 25, 2014

(65) Prior Publication Data

US 2014/0277040 A1 Sep. 18, 2014

Related U.S. Application Data

(60) Provisional application No. 61/783,436, filed on Mar. 14, 2013.

(51) Int. Cl.
*A61B 17/32* (2006.01)

(52) U.S. Cl.
CPC .............. *A61B 17/32002* (2013.01); *A61B 2017/320064* (2013.01)

(58) Field of Classification Search
CPC ............ A61B 17/1613–17/1633; A61B 17/320016–17/32002; A61B 17/320758; A61B 2017/320024–2017/320032; A61B 2017/320766–2017/320775
USPC .............. 606/159, 167, 170, 179, 180
See application file for complete search history.

(56) References Cited

U.S. PATENT DOCUMENTS

| | | | |
|---|---|---|---|
| 4,646,738 A | 3/1987 | Trott | |
| 4,983,179 A | 1/1991 | Sjostrom | |
| 5,084,052 A | 1/1992 | Jacobs | |
| 5,217,479 A | 6/1993 | Shuler | |
| 5,269,798 A | 12/1993 | Winkler | |
| 5,366,468 A | 11/1994 | Fucci et al. | |
| 5,489,291 A | 2/1996 | Wiley | |
| 5,492,527 A | 2/1996 | Glowa et al. | |
| 5,592,727 A | 1/1997 | Glowa et al. | |
| 5,601,583 A | 2/1997 | Donahue et al. | |
| 5,620,447 A | 4/1997 | Smith et al. | |
| 5,693,063 A | 12/1997 | Van Wyk et al. | |
| 5,759,185 A | 6/1998 | Grinberg | |
| 5,766,199 A | 6/1998 | Heisler et al. | |

(Continued)

FOREIGN PATENT DOCUMENTS

| | | |
|---|---|---|
| AU | 3781400 A | 7/2000 |
| EP | 0 796 064 A1 | 9/1997 |

(Continued)

OTHER PUBLICATIONS

"The Formula for Success" brochure dated 2007 (6 pages).

*Primary Examiner* — Victor Nguyen
*Assistant Examiner* — Jonathan Hollm
(74) *Attorney, Agent, or Firm* — Flynn, Thiel, Boutell & Tanis, P.C.

(57) ABSTRACT

A surgical tool arrangement for performing endoscopic surgical procedures which includes a powered handpiece and a cutting accessory which detachably connects to the handpiece and incorporates a cutting head configuration which provides both aggressive tissue resection and a smooth-cut finish on treated tissue.

21 Claims, 12 Drawing Sheets

(56) References Cited

U.S. PATENT DOCUMENTS

| | | |
|---|---|---|
| 5,833,692 A | 11/1998 | Cesarini et al. |
| 5,833,702 A | 11/1998 | Van Wyk et al. |
| 5,843,106 A | 12/1998 | Heisler |
| 5,851,208 A | 12/1998 | Trott |
| 5,913,867 A | 6/1999 | Dion |
| 6,001,116 A | 12/1999 | Heisler et al. |
| 6,053,928 A | 4/2000 | Van Wyk et al. |
| 6,217,598 B1 | 4/2001 | Berman et al. |
| 6,312,438 B1 | 11/2001 | Adams |
| 6,312,441 B1 | 11/2001 | Deng |
| 6,620,180 B1 | 9/2003 | Bays et al. |
| 6,827,725 B2 | 12/2004 | Batchelor et al. |
| 7,237,990 B2 | 7/2007 | Deng |
| 7,618,428 B2 | 11/2009 | O'Quinn et al. |
| 7,682,333 B2 | 3/2010 | Deng |
| 7,803,170 B2 | 9/2010 | Mitusina |
| 7,887,559 B2 | 2/2011 | Deng et al. |
| 8,062,319 B2 | 11/2011 | O'Quinn et al. |
| 2003/0135151 A1 | 7/2003 | Deng |
| 2004/0092991 A1 | 5/2004 | Deng |
| 2004/0220602 A1 | 11/2004 | Deng et al. |
| 2005/0065538 A1 | 3/2005 | Van Wyk |
| 2005/0222598 A1* | 10/2005 | Ho ............ A61B 17/32 606/171 |
| 2006/0142775 A1 | 6/2006 | Heneberry et al. |
| 2006/0196038 A1* | 9/2006 | Van Wyk ......... A61B 17/32002 29/557 |
| 2006/0212060 A1* | 9/2006 | Hacker ............ A61B 17/32001 606/180 |
| 2008/0208194 A1* | 8/2008 | Bickenbach ..... A61B 17/32002 606/79 |
| 2010/0298855 A1 | 11/2010 | Dierck |
| 2011/0238099 A1 | 9/2011 | Loreth |
| 2012/0203230 A1 | 8/2012 | Adams |

FOREIGN PATENT DOCUMENTS

| | | |
|---|---|---|
| EP | 0 800 793 A1 | 10/1997 |
| EP | 0 836 833 A2 | 4/1998 |
| EP | 1006 898 B1 | 6/2000 |
| EP | 1 253 863 B1 | 11/2002 |
| EP | 1 676 537 A1 | 7/2006 |
| EP | 1 702 573 A1 | 9/2006 |
| WO | WO 00/78236 A1 | 12/2000 |
| WO | WO 01/05313 A1 | 1/2001 |
| WO | WO 2006/102124 A2 | 9/2006 |

* cited by examiner

SURGICAL TOOL ARRANGEMENT AND SURGICAL CUTTING ACCESSORY FOR USE THEREWITH

CROSS REFERENCE TO RELATED APPLICATION

This claims the benefit of U.S. Provisional Application Ser. No. 61/783,436, filed Mar. 14, 2013, which is incorporated herein by reference in its entirety.

FIELD OF THE INVENTION

This invention generally relates to a surgical tool arrangement useful for performing endoscopic surgical procedures which includes a powered handpiece and, more particularly, to a cutting accessory which detachably connects to the handpiece and incorporates a cutting head configuration which provides both aggressive tissue resection and a smooth-cut finish on treated tissue.

BACKGROUND OF THE INVENTION

Endoscopic surgical procedures are routinely performed in order to accomplish various surgical tasks. In such a surgical procedure, small incisions or portals are made in the patient. An endoscope, which is a device that allows medical personnel to view the surgical site, is inserted into one of the portals. Surgical instruments used to perform other tasks are inserted into other portals. The surgeon views the surgical site through the endoscope to determine how to manipulate the surgical instruments in order to accomplish the desired procedure. An advantage of performing endoscopic surgery is that, since the portions of the body that are cut open are minimized, the portions of the body that need to heal after the surgery are likewise reduced. Moreover, during an endoscopic surgical procedure, only relatively small portions of the patient's internal organs and tissue are exposed to the open environment. This minimal opening of the patient's body lessens the extent to which a patient's organs and tissue are open to infection.

The ability to perform endoscopic surgery is enhanced by the development of powered surgical tools especially designed to perform such procedures. Once such tool is sold by the Assignee hereof under the trademark FORMULA®. This tool is in the form of a cylindrical handpiece designed to be held in the hand of the surgeon. The handpiece has a front or distal end provided with a coupling assembly for releasably holding a cutting accessory, and a motor disposed within a handpiece housing which drives the accessory. One such cutting accessory, often termed a "shaver", includes a hub which defines the proximal end of the accessory and is appropriately configured to cooperate with the coupling assembly of the handpiece to lock the accessory thereto, an elongated and tubular housing element having a proximal end fixed to the hub, and an elongated cutting element including a drive shaft disposed within the housing element. When the accessory is attached to the handpiece, the handpiece motor couples to the drive shaft of the accessory and moves same relative to the outer housing element. The handpiece motor is selectively actuable to drive the accessory drive shaft so as to cause a desired cutting action at the distal end of the accessory. The handpiece is associated with a control unit which controls the functioning thereof, and is actuated by the user via appropriate buttons provided on the handpiece itself, or alternatively directly at the control unit.

In an endoscopic surgical procedure, irrigating fluid is introduced into the surgical site. This fluid serves as a transport media for removing tissue and debris from the surgical site. In order to remove the irrigating fluid and the material contained therein, the above handpiece and the various accessories which are usable therewith together define a suction conduit. A suction pump is connected to the handpiece to provide the suction force needed for drawing the fluid and material away from the surgical site. In order to control the suction flow through the accessory and the handpiece, the handpiece is provided with a manually operated valve which is manipulated by the surgeon to control suction of material away from the surgical site.

Mechanical cutting accessories, such as the shaver discussed above, are commonly used in arthroscopic procedures, and allow for the resection of hard and soft bodily tissues, for example, those found within the knee, shoulder and other joints. In such a cutting accessory, the outer housing element defines a window or opening at the distal end, which window is defined by an edge of the wall of the outer housing element. The cutting element drive shaft at the distal end thereof also includes a cutting head having a window defined by an edge of the wall of the cutting head, and when the cutting head is disposed within the housing element, the cutting head window is positioned adjacent the window of the housing element. As the drive shaft is moved relative to the housing element by the handpiece motor, the cutting edge of the cutting head window and the opposed and facing cutting edge of the housing element window cause a cutting action which effectively severs tissue located within the housing element window and between the opposed cutting edges of the housing element and the cutting head. The configurations of these opposed edges allow for removal of particular tissue types, and a variety of different cutting window geometries are available to specifically address the type of cutting the accessory is to carry out. For example, providing the windows of both of the housing element and cutting head with straight cutting edges is useful for making fine or detailed cuts and removing areas of hard tissue, such as bone. This arrangement is often called a "straight-on-straight" cutting style or action. Alternatively, providing the windows of both the housing element and cutting head with toothed or serrated cutting edges achieves a more aggressive cut and is useful for removal of soft fibrous tissue, which arrangement is often called a "tooth-on-tooth" cutting style. A further arrangement involves providing the window of the housing element with a straight cutting edge and the window of the cutting head with a toothed cutting edge, which is often called a "tooth-on-straight" cutting style. Thus, a surgeon may often need to switch cutting accessories during a procedure in order to carry out the appropriate type or style of cut.

While the above-described surgical accessories have proven useful, when a change in cutting is desired, these accessories require the user to remove the accessory currently in use from the patient, to remove the accessory from the handpiece, install a different accessory onto the handpiece, and then reinsert the new accessory into the surgical site. Further, the known arrangements require the purchase of a multitude of accessories, which results in higher costs and a larger number of surgical accessories which must be present in the operating room in order to carry out the desired surgical procedure.

The predominant function of teeth provided on a cutting accessory, and specifically the teeth provided on the cutting head of the inner cutting element, is to pull tissue towards the cutting edge of the outer housing element, at which point the tissue is cut by means of a scissoring action between the two respective cutting edges. Even if the cutting edge of the window formed in the outer housing element is straight, the teeth of the cutting head of the inner cutting element can leave a jagged-cut finish on the tissue and/or can make grooves in the tissue. To create the cleanest finish on the tissue, the straight-on-straight scissoring or cutting style as mentioned above is typically required. However, this means that the ability of the inner cutting element to pull tissue to the cutting edge of the outer housing element is limited, which can significantly reduce the consumption rate of the surgical accessory.

In order to obviate or at least minimize disadvantages of known arrangements, the surgical accessory according to the invention provides aggressive tissue resection while still providing a smooth-cut finish on tissue resected during surgery. In this regard, the cutting window or windows located at the distal end of the cutting accessory is/are provided with alternating toothed and straight cutting edges which facilitates both aggressive and smooth cutting in one surgical cutting accessory.

Providing this type of blade geometry on a surgical accessory allows the surgeon, with a single surgical cutting accessory, to achieve a very smooth-cut finish on tissue while still being able to aggressively remove soft tissue. As such, the arrangement according to the invention reduces the number of surgical accessories that are needed during a surgery to achieve the desired result, and accordingly minimizes the need to remove the surgical accessory from the patient and then from the handpiece in order to replace same with another surgical accessory, all of which can save time during a procedure, promote safety during the procedure and reduce overall equipment costs.

Figure 1:
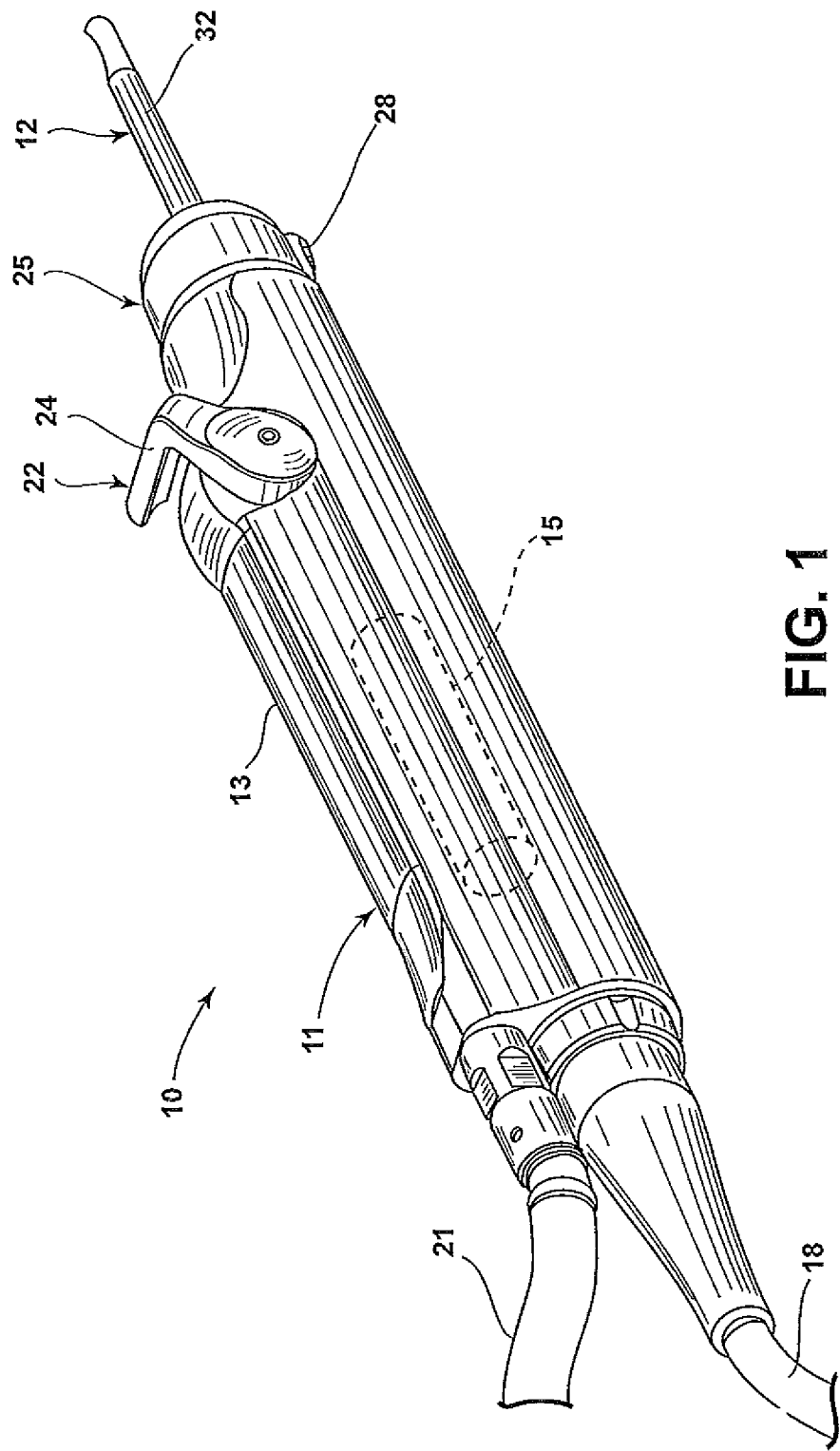
FIG. 1 is a perspective view of the surgical tool arrangement according to the invention, including a handpiece with a surgical accessory attached thereto.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction toward the end of the arrangement which is furthest from the patient. Said terminology will include the words specifically mentioned, derivatives thereof, and words of similar import.

DETAILED DESCRIPTION

Figure 2:
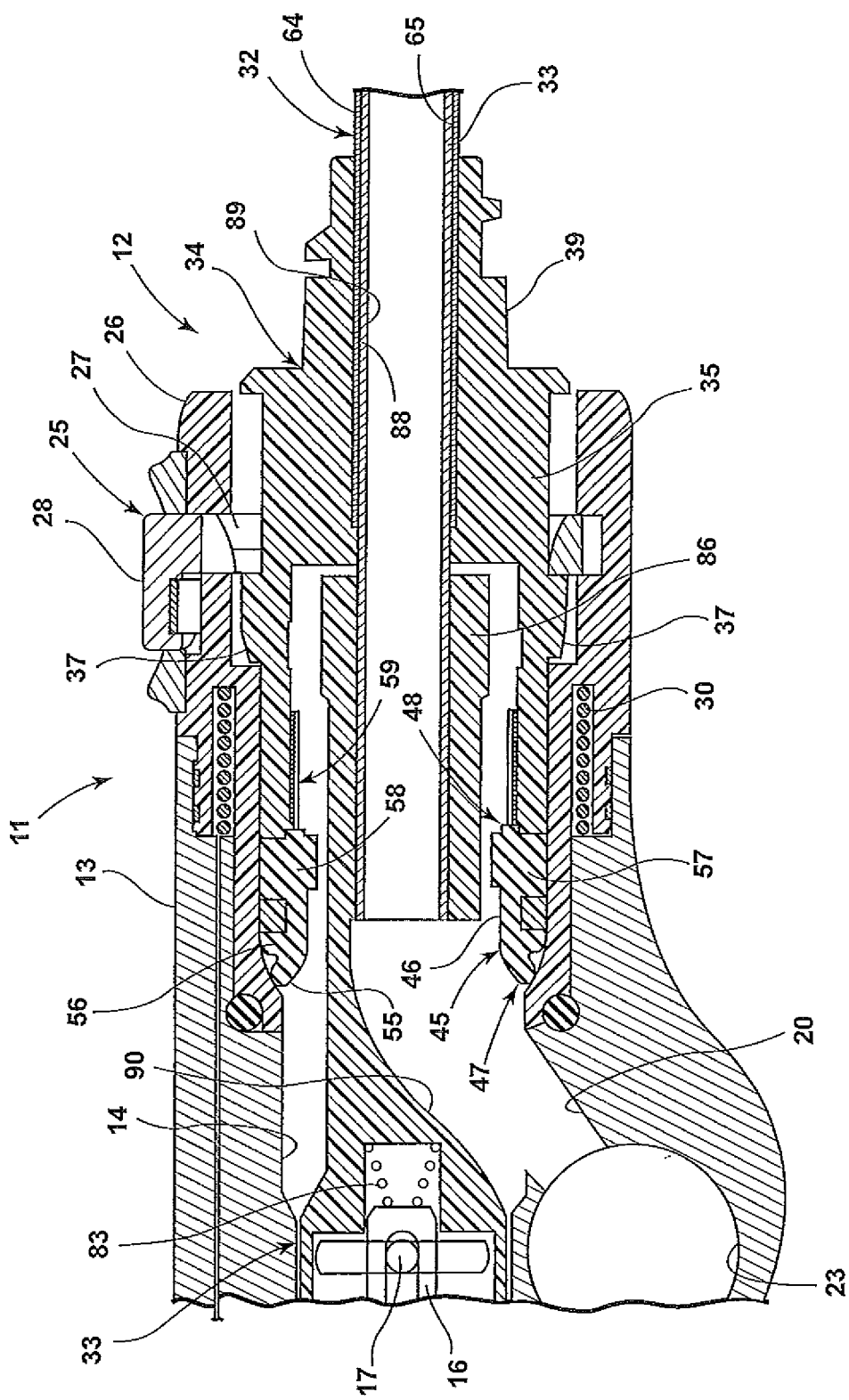
FIG. 2 is an enlarged, fragmentary longitudinal cross-sectional view of the handpiece of FIG. 1 with the surgical accessory attached thereto.

Referring to FIGS. 1 and 2, a surgical tool arrangement 10 according to the invention is illustrated. The arrangement 10 includes a handpiece 11, which at its distal end mounts thereon a surgical accessory 12.

Handpiece 11 is a commercially available surgical handpiece manufactured by the Assignee hereof, under Model Nos. 375-704-500 and 375-701-500, and is accordingly only briefly described herein. Handpiece 11 includes an elongate outer housing 13 defining an elongate bore 14 therein. A motor 15 (shown diagrammatically only in FIG. 1) is disposed within housing bore 14. Motor 15 includes an output or drive shaft 16, which drive shaft 16 mounts a drive pin 17 at the distal end thereof. A power cable 18 is coupled to the proximal end of handpiece 11 for supplying power to motor 15.

Handpiece housing 13 defines therein an elongate suction bore (not shown) extending generally parallel to and sidewardly of housing bore 14. This suction bore communicates with a diagonally extending suction passage 20 defined in housing 13, which passage 20 provides communication between the distal end of housing bore 14 and the suction bore. Suction is drawn through the handpiece 11 by a suction pump (not shown), which is connected to the handpiece 11 via a suction tube 21. Suction flow through the handpiece 11 is regulated by an adjustable valve 22 having a valve stem (not shown) which is movably mounted in a valve bore 23 defined in housing 13. The valve 22 is adjusted by the user via a movable handle or arm 24 connected to the valve stem. The above handpiece suction arrangement is described in detail in U.S. Pat. No. 7,682,333 issued on Mar. 23, 2010, which patent is owned by the same Assignee hereof and is hereby incorporated by reference herein in its entirety.

The accessory 12 is removably attached to the distal end of the handpiece 11 by a coupling assembly 25 provided on the handpiece 11. Coupling assembly 25 includes a generally ring-shaped collet 26 secured to the distal end of the handpiece housing 13. A locking ring 27 is movably disposed in collet 26 and is biased to hold the accessory 12 within the housing bore 14 of handpiece 11. A release button 28 is provided on locking ring 27, and is used to release the locking ring 27 and allow removal of the accessory 12 from handpiece 11. Further, a coil 30 is provided in collet 26, which is used to facilitate inductive signal transfer to/from a radio-frequency identification device (RFID) disposed in the accessory 12 as discussed below.

Figure 3:
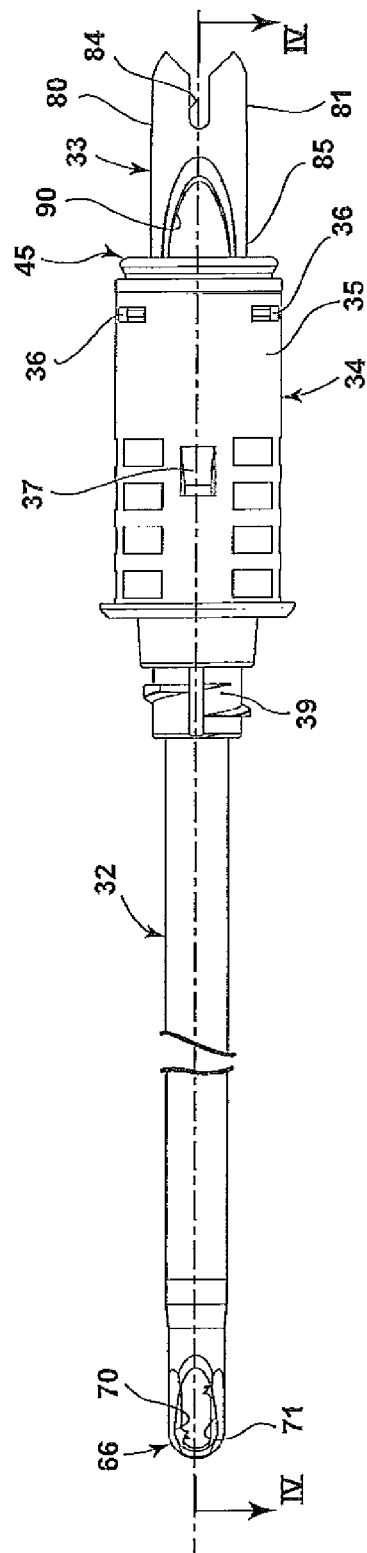
FIG. 3 is an enlarged top and fragmentary view of the surgical accessory.
Figure 4:
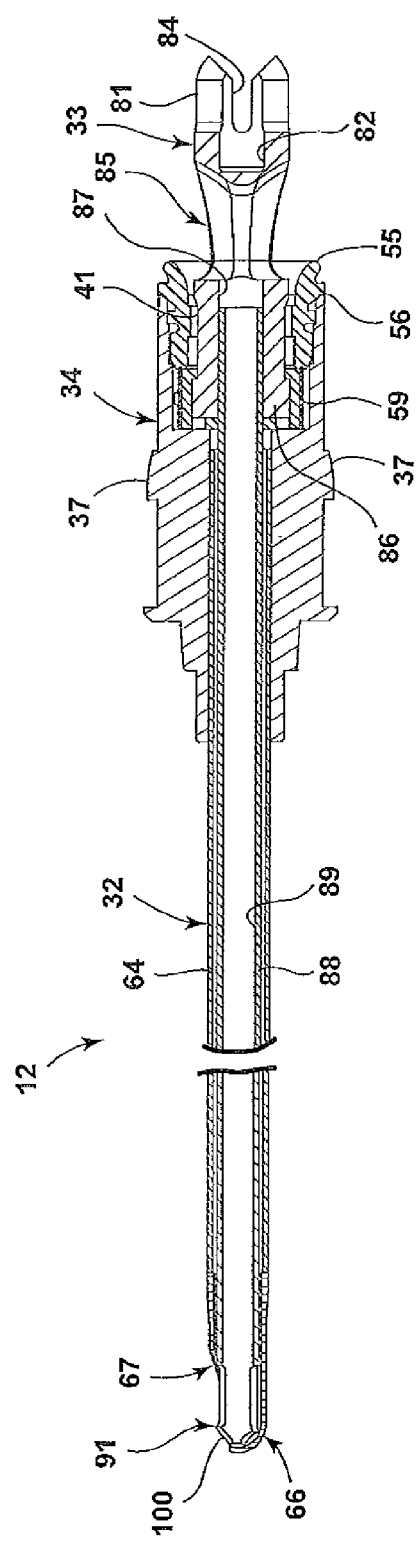
FIG. 4 is an enlarged longitudinal cross-sectional and fragmentary view of the surgical accessory of FIG. 3, as seen generally along line IV-IV in FIG. 3.
Figure 5:
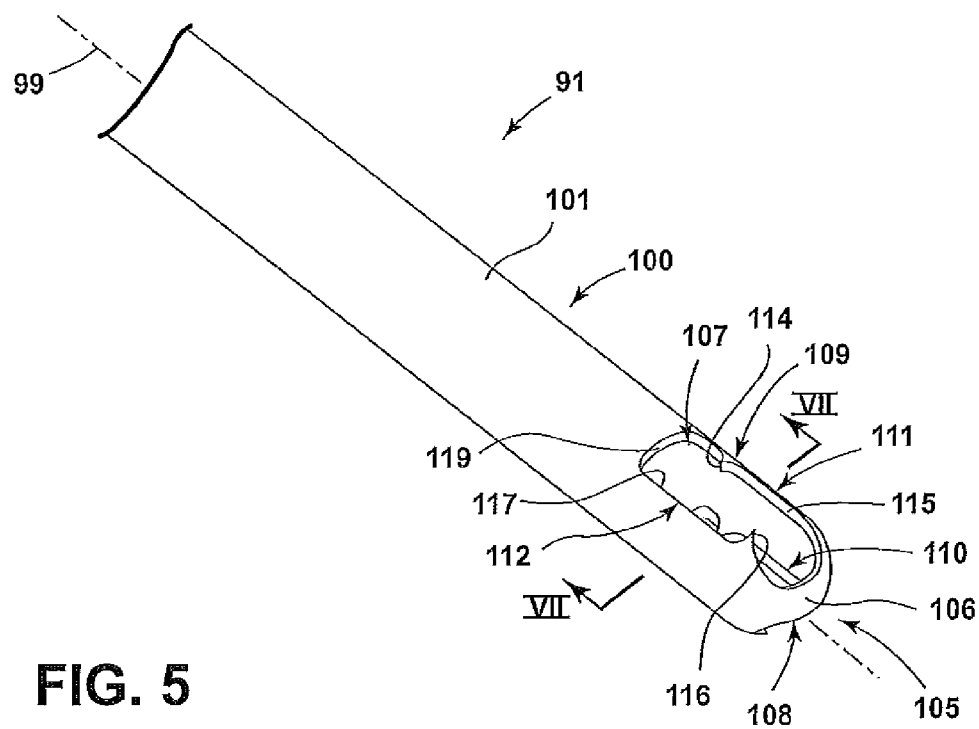
FIG. 5 is an enlarged perspective and fragmentary view of a first embodiment of a cutting head of the surgical accessory in isolation.

Referring to FIGS. 2-4, the accessory 12 will now be described. Accessory 12 includes an outer cannula or tubular housing element 32 and a cutting element 33 disposed within housing element 32. Housing element 32 includes a hub 34 which defines the proximal end thereof. Hub 34 is defined by a generally tubular base body 35, which defines therein a pair of generally rectangular and diametrically-opposed openings 36 adjacent the proximal end thereof. Base body 35 also has formed thereon a pair of outwardly-projecting, diametrically opposed and generally ramp-shaped ears 37 disposed distally of openings 36. Ears 37 cooperate with coupling assembly 25 of handpiece 11 to secure accessory 12 therein. Hub 34 has a distal end defined by a head 39 or nose of a reduced diameter as compared to base body 35. In the illustrated embodiment, a thread 40 extends about the circumference of head 39, which thread 40 may be used to attach an operating cannula (not shown) over housing element 32. Further, hub 34 defines therein a bore 41 which extends completely through the hub 34, and with which openings 36 of base body 35 communicate.

An annular seal 45 is disposed within the proximal end of bore 41 of hub 34. Seal 45 is constructed of a resilient elastomeric material, and is defined by a main section 46 and axially-spaced proximal and distal sections 47 and 48 disposed at respective opposite ends of the main section 46. Proximal section 47 defines thereon a pair of annular ribs 55 and 56, which are disposed in sealing engagement with an inner annular surface of the collet 26 of the handpiece 11 when accessory 12 is coupled thereto, as shown in FIG. 2. Distal section 48 defines thereon a pair of outwardly projecting and diametrically-opposed lock tabs 57 which engage within the respective openings 36 of hub 34 to secure the seal 45 to the hub 34 and fix the axial position of seal 45 relative thereto. Distal section 48 additionally defines thereon a pair of inwardly projecting and diametrically-opposed stop tabs 58, which are generally radially aligned with the respective lock tabs 57. As shown in FIGS. 2 and 4, an RFID device 59 encapsulated within a ring structure is located within hub bore 41 distally from, and in axially-adjacent relationship with, the distal section 48 of seal 45.

The above-described coupling arrangement of handpiece 11 and the arrangement of the encapsulated RFID device 59 and coil 30 are disclosed in U.S. Pat. No. 7,887,559 issued on Feb. 15, 2011, which patent is owned by the same Assignee hereof and is hereby incorporated by reference herein in its entirety.

Figure 13:
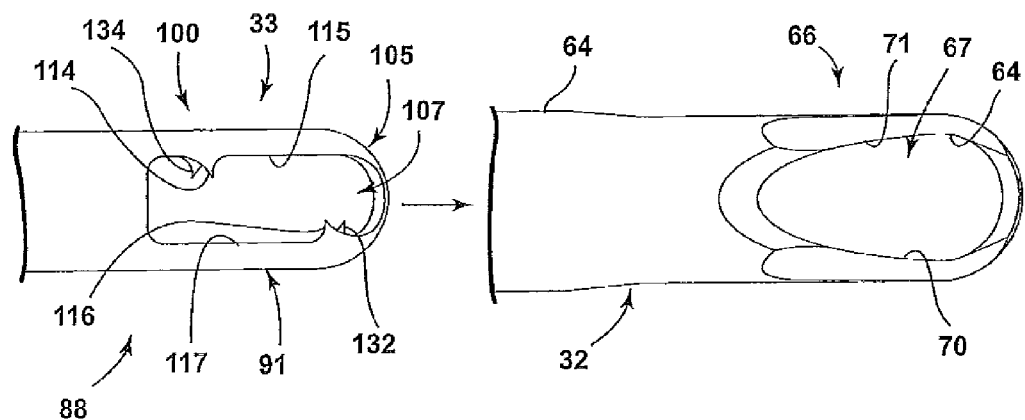
FIG. 13 is an enlarged, fragmentary and exploded top view of the of distal ends of the outer housing element and the cutting head of the inner cutting element of the surgical accessory of FIG. 3.
Figure 14:
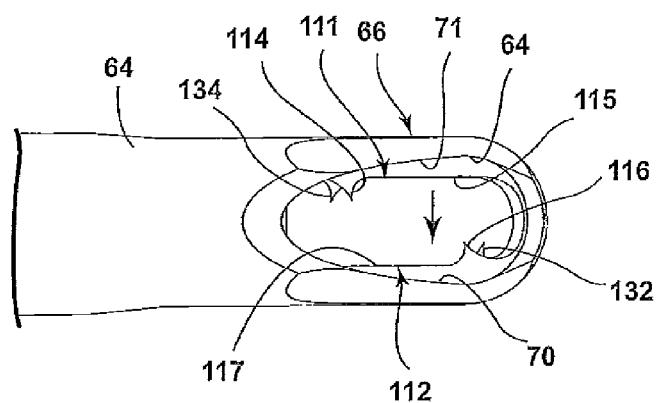
FIG. 14 is an enlarged and fragmentary top view of the distal end of the surgical accessory of FIG. 3.
Figure 15:
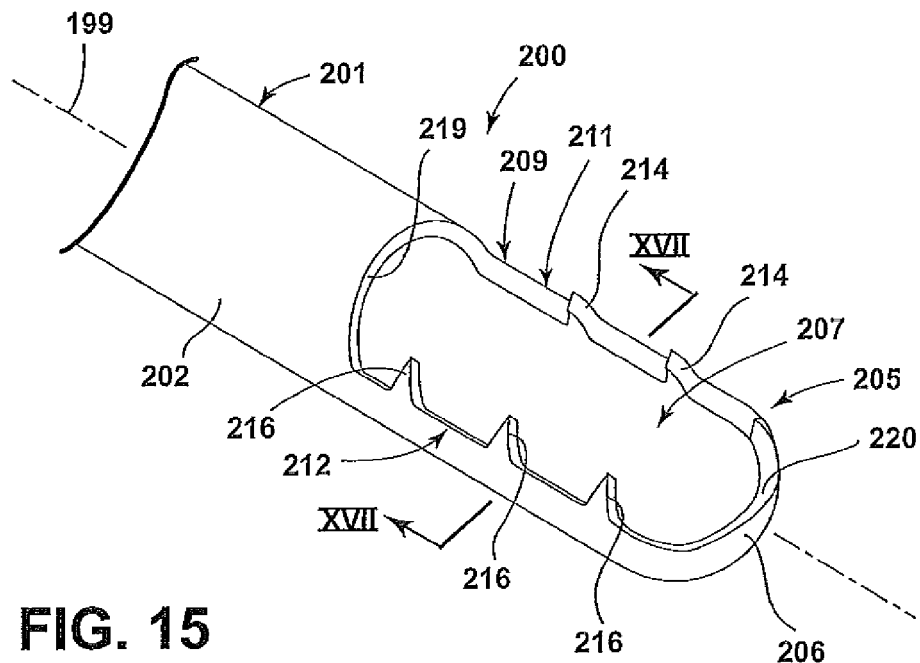
FIG. 15 is an enlarged and fragmentary perspective view of a second embodiment of the cutting head of the surgical accessory in isolation.

Housing element 32 additionally includes an elongate housing tube 64 which projects distally from hub 34. More specifically, housing tube 64 has a proximal end which is fixedly mounted within the distal portion of bore 41 of hub 34. Housing tube 64 defines an elongate bore or conduit 65 therein, in which the cutting element 33 is disposed as discussed below. As best shown in FIGS. 13 and 14, housing tube 64 has a distal end 66 which is cut so as to define a window 67, which window 67 in the illustrated embodiment opens generally sidewardly of the tube 64, such that the distal end 66 is generally closed in the axial direction. The cutting of the housing tube 64 results in a ring-shaped edge of housing tube 64 which defines cutting window 67, which edge has circumferentially-spaced, opposed and generally longitudinally-extending sides 70 and 71. In the illustrated embodiment, both of these sides 70 and 71 are non-toothed. More specifically, the sides 70 and 71 of window 67, as same extend longitudinally, have generally straight or linear central regions and curved end regions on opposite axial sides of the respective central region.

Turning now to the cutting element 33, same includes a hub 80 which defines the proximal end thereof. Hub 80 incorporates a motor-engaging drive element 81 defining a proximally opening bore 82 therein in which a coil spring 83 (shown only in FIG. 2) is located, and a slot 84 which extends transversely to the longitudinal axis of the cutting element 33. The hub 80 additionally includes a neck 85 which projects distally from drive element 81. Neck 85 terminates at a head 86 which has an enlarged outer diameter as compared to the remainder of the neck 85. In this regard, the outer diameter of the head 86 is slightly larger than the inward projection of the respective stop tabs 58 of seal 45. A bore 87 extends through the neck 85 and the head 86, in which an elongate and tubular drive shaft 88 is fixed. Drive shaft 88 defines therein a suction passage 89 which is in communication with a suction port 90 defined in the neck 85, which suction port 90 is in turn in communication with the suction passage 20 of handpiece 11.

Drive shaft 88 has a distal end 91 which defines a cutting head 100 of the cutting element 33. In the illustrated embodiment, the drive shaft 88 and the cutting head 100 are constructed as an integral or one-piece member formed from rigid metal, such as stainless steel. Alternatively, the drive shaft 88 and the cutting head 100 may be provided as separate components which are fixed to one another. In this regard, the drive shaft 88 may be constructed of a rigid plastic and then induction welded to the cutting head 100, which may be constructed of rigid metal, such as stainless steel.

Figure 12:
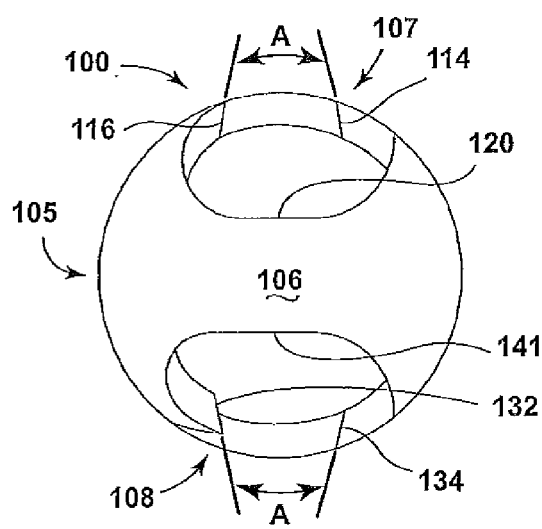
FIG. 12 is an enlarged end view of the distal end of the cutting head of FIG. 5, as seen generally along line XII-XII in FIG. 6.

With reference to FIGS. 5-11, the cutting head 100 defines a central longitudinal axis 99 and includes a tubular shaft 101, which shaft 101 in the illustrated embodiment is coextensive with the drive shaft 88. The shaft 101 is defined by a cylindrical wall 102 which encloses a hollow interior 103. The shaft 101 has a distal end 105 defining a bearing wall 106 which extends transversely relative to the axis 99. In the illustrated embodiment, the distal end 105 is cut so as to define a pair of windows or openings 107 and 108 which are located diametrically opposite one another along opposite sides of the cutting head 100. The windows 107 and 108 open generally sidewardly of the cutting head 100, and extend in the distal direction of the cutting head 100 up to the bearing wall 106, which bearing wall 106 (as best shown in FIG. 12) extends transversely between the windows 107 and 108 and defines the distal-most extent of each of the windows 107 and 108. The bearing wall 106 as such partially closes off the distal end 105 of the drive shaft 88.

Figure 6:
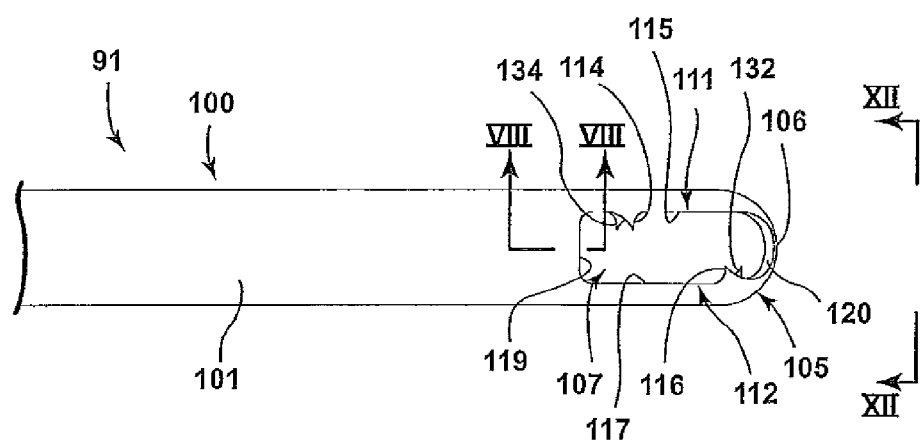
FIG. 6 is an enlarged top and fragmentary view of the cutting head of FIG. 5.

The cutting of the distal end 105 of the cutting head 100 results in a pair of ring-shaped edges 109 and 110 which respectively define the cutting windows 107 and 108. The upper ring-shaped edge 109 of the cutting window 107 shown in FIGS. 5 and 6 has circumferentially-spaced, opposed and generally longitudinally-extending sides 111 and 112. The side 111 of the cutting window 107 is partially serrated or toothed, and in the illustrated embodiment includes a tooth 114. The side 111 of cutting window 107 additionally includes a substantially straight-edged portion 115 disposed directly adjacent the tooth 114 and extending distally away therefrom towards the bearing wall 106. The opposite side 112 of the window 107 is partially serrated or toothed, and similar to the side 111 includes a tooth 116 and a substantially straight-edged portion 117 disposed directly adjacent the tooth 116. The ring-shaped edge 109 of cutting window 107 additionally includes a proximal portion 119 which extends between and interconnects the proximal regions of the sides 111 and 112, and a distal portion 120 which extends between and interconnects the distal regions of the sides 111 and 112 and defines an upper edge of the bearing wall 106. As best shown in FIG. 6, the tooth 114 and straight-edged portion 115 on one side 111 of the window 107 are respectively aligned (in a direction transverse to the axis 99) with the straight-edged portion 117 and the tooth 116 on the opposite side 112 of the window 107. Further, in the illustrated embodiment, the straight-edged portions 115 and 117 are generally parallel with one another and with the axis 99.

Figure 10:
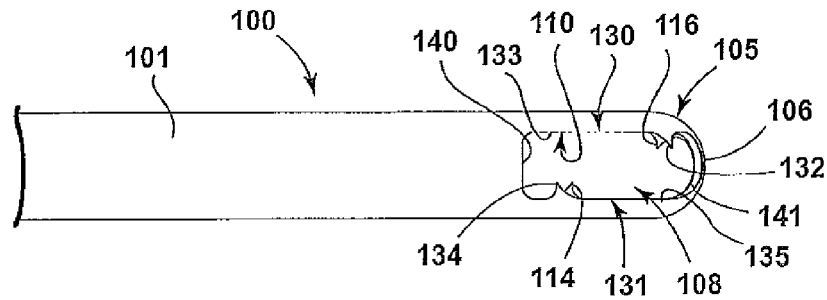
FIG. 10 is an enlarged bottom and fragmentary view of the cutting head of FIG. 5, rotated approximately 180 degrees from the view in FIG. 6.
Figure 11:
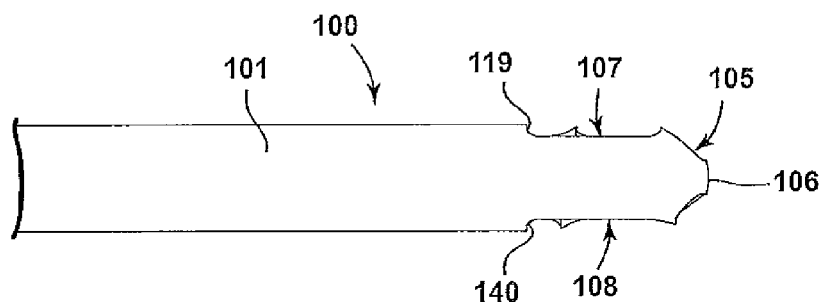
FIG. 11 is an enlarged side and fragmentary view of the cutting head of FIG. 5.

With reference to FIG. 10 which shows the opposite side of the cutting head 100 from that shown in FIG. 6, the lower ring-shaped edge 110 of the cutting window 108 is configured similarly to upper edge 109. Specifically, the lower ring-shaped edge 110 has circumferentially-spaced, opposed and generally longitudinally-extending sides 130 and 131. The side 130 of the cutting window 108 is partially serrated or toothed, and in the illustrated embodiment includes a tooth 132. The side 130 of cutting window 108 additionally includes a substantially straight-edged portion 133 disposed directly adjacent the tooth 132 and extending proximally away therefrom. The opposite side 131 of the window 108 is partially serrated or toothed, and includes a tooth 134 and a substantially straight-edged portion 135 disposed directly adjacent the tooth 134. The ring-shaped edge 110 of cutting window 108 additionally includes a proximal portion 140 which extends between and interconnects the proximal regions of the sides 130 and 131, and a distal portion 141 which extends between and interconnects the distal regions of the sides 130 and 131 and defines a lower edge of the bearing wall 106. With continued reference to FIG. 10, the tooth 132 and straight-edged portion 133 on one side 130 of the window 108 are respectively aligned (in a direction transverse to the axis 99) with the straight-edged portion 135 and the tooth 134 on the opposite side 131 of the window 108. Further, in the illustrated embodiment, the straight-edged portions 133 and 135 are generally parallel with one another and with the axis 99. Additionally, as shown in FIGS. 6 and 10, in this embodiment, the teeth 114 and 116 of upper cutting window 107 are respectively vertically aligned with the teeth 134 and 132 of the lower cutting window 108.

Figure 7:
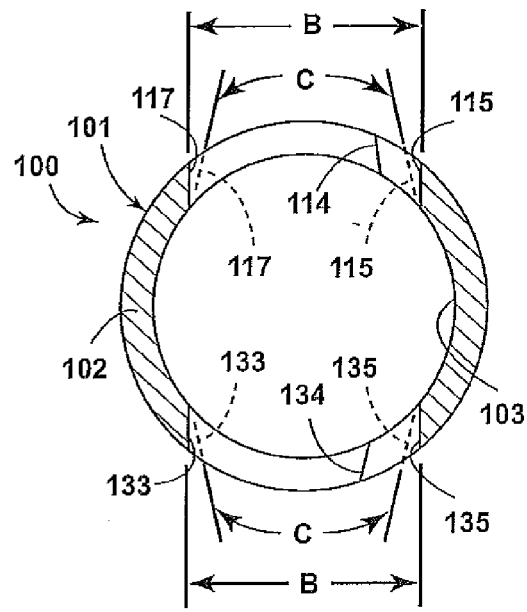
FIG. 7 is an enlarged cross-sectional view as seen generally along line VII-VII in FIG. 5.
Figure 8:
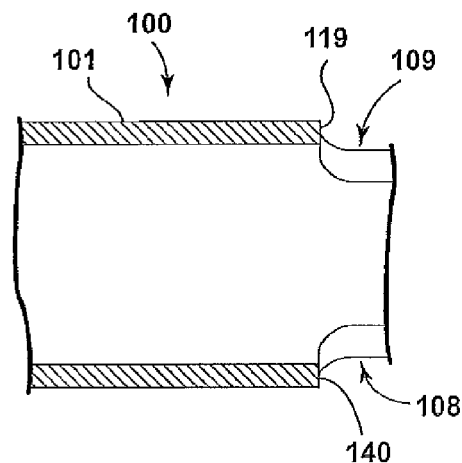
FIG. 8 is an enlarged cross-sectional and fragmentary view as seen generally along line VIII-VIII in FIG. 6.
Figure 9:
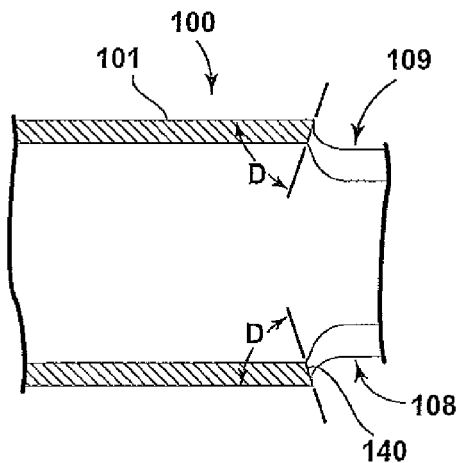
FIG. 9 is an enlarged cross-sectional and fragmentary view similar to FIG. 8, but illustrating an alternative edge configuration of the proximal edge portion of the cutting window of the cutting head of FIG. 5.

The upper and lower cutting windows 107 and 108 of the cutting element 33 are provided with geometries, and specifically shear angles, which maximize the cutting ability of the cutting element 33. Shear angle in this context is intended to refer to the opening angle of the windows 107 and 108 which is determined during the cutting process which forms the windows 107 and 108. In this regard, the ring-shaped edges 109 and 110 may be cut so as to provide some, or alternatively all, cutting edges with a negative internal shear angle which is less than zero degrees. This negative shear angle, when applied to cutting edges such as the teeth 114, 116, 132 and 134, increases the likelihood that tissue will be scooped into the cutting windows 107 and 108, thereby increasing the consumption rate of the cutting accessory. In the illustrated embodiment as shown in FIG. 12, at least the internal faces of the teeth 114, 116, 132 and 134 are provided with an internal shear angle A, which angle A is less than zero degrees. Further, as shown in FIG. 7, the internal faces of the respective straight-edged portions 115, 117, 133 and 135 in the illustrated embodiment have an internal shear angle B which is greater than or equal to zero degrees. However, as shown in dotted lines in FIG. 7, the internal faces of straight-edged portions 115, 117, 133 and 135 can alternatively be provided with an internal shear angle C which is negative, or less than zero degrees, similar to the teeth 114, 116, 132 and 134. Providing the teeth and/or straight-edged portions with negative shear angles means that the internal cutting face of each of these components, when viewed in a direction normal to the axis 99, angles inwardly as same projects towards the axis 99. Additionally, the proximal internal faces of the proximal edges 119 and 140 of the windows 107 and 108 in the illustrated embodiment as shown in FIG. 8 can be provided with a shear angle which is greater than or equal to zero degrees. Alternatively, the internal faces of the edges 119 and 140 can be provided with a negative shear angle D which is less than zero degrees, as shown in FIG. 9. Providing the proximal edges 119 and 140 with a negative shear angle reduces the likelihood that tissue will snag and cause the cutting accessory to clog.

Figure 7A:
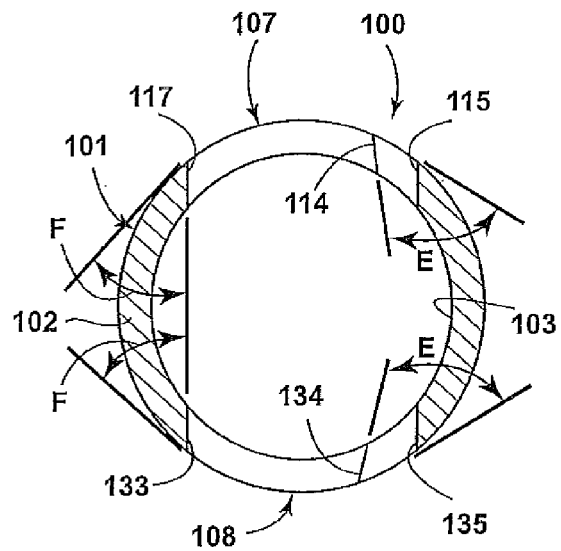
FIG. 7A is a cross-sectional view identical to FIG. 7 but referencing additional features.

Additionally, the cutting head 100 utilizes small included edge angles on the cutting edges thereof. Included edge angle is the angle of the cutting edge as measured between a line tangential to the outer surface of the cutting head 100 and a line parallel with the internal face of the respective cutting edge. More specifically, as shown in FIG. 7A, the included edge angle E of the teeth (only teeth 114 and 134 are shown in FIG. 7A, but it is to be understood that the teeth 116 and 132 also have the included edge angle E), and the included edge angle F of the straight-edged portions (only straight-edged portions 117 and 133 are labeled in FIG. 7A, but it is to be understood that straight-edged portions 115 and 135 also have the included edge angle F) of the windows 107 and 108 are each acute, or less than 90 degrees. The smaller the included edge angle, the more likely that tissue will be cut by the respective cutting edge. Creation of the internal shear angles and the included edge angles as discussed above in the illustrated embodiment is formed by a laser-cutting process.

The cutting element 33 is assembled to the outer tubular housing element 32 by inserting the distal end 91 of the cutting element 33 into the bore 41 at the proximal end of the hub 34. During this insertion, the enlarged head 86 of hub 80 expands the seal 45 and the head 86 pushes past the stop tabs 58, at which point the seal 45 essentially resumes its original shape. The stop tabs 58, while allowing some axial displacement of the cutting element 33 relative to housing element 32, prevent the cutting element 33 from detaching or falling out of the housing element 32 due to gravitational forces.

The assembled accessory 12 is secured to the handpiece 11 in a similar manner to that described in the '559 patent referenced above, and will accordingly be only briefly described here. The accessory 12 is attached to the handpiece 11 by inserting the hubs 34 and 80 into the open distal end of collet 26. The ears 37 of hub 34 seat within collet 26, and the locking ring 27 serves to hold the accessory 12 within the handpiece 11. The above securement of the accessory 12 to handpiece 11 causes the drive element 81 to engage the motor output shaft 16. More specifically, the drive pin 17 of output shaft 16 seats within the slot 84 of drive element 81, such that the rotational movement of the output shaft 16 is transferred to the cutting element 33. The spring 83 of drive element 81 biases the cutting element 33 forwardly or in the distal direction, so as to maintain the distal end 91, and specifically the bearing wall 106, of cutting element 33 in bearing contact with the interior of the closed distal end 66 outer housing element 32.

In operation, the distal end of the tool 10 is inserted into the surgical site. If desirable or necessary, the distal end of the tool 10 can be inserted into the surgical site through a working portal defined by a conventional cannula or trocar (not shown). The cutting element 33 is controlled by a control unit (not shown) connected to the handpiece cable 18, which control unit supplies electrical power to the motor 15 of the handpiece 11 in order to actuate the cutting element 33. Control unit also controls the mode of operation of the cutting element 33, for example by controlling motor 15 so as to drive cutting element 33 in a forward or reverse direction, or in an oscillating manner. If cutting of tissue is desired, then the motor 15 is activated so as to cause the cutting element 33 to rotate within and relative to the outer housing element 32. In this regard, it will be appreciated that the control unit may include appropriate control buttons so as to allow the surgeon or operator to select the desired accessory operations. These control functions of the cutting element 33 may alternatively be performed directly from the handpiece 11 which would then include the appropriate control buttons thereon. Alternatively, the control unit may be associated with a switch, either through a suitable cable or wirelessly, to allow the surgeon to operate the controls remotely. Such a switch may be a footswitch or a hand switch.

As shown in FIG. 14, with the cutting element 33 disposed within the housing element 32 and the accessory 12 secured to handpiece 11 as described above, when the cutting element 33 is rotated by the handpiece motor 15 in the direction indicated by the arrow in FIG. 14, the side 111 of the upper window 107 of cutting element 33 moves towards the side 70 of the housing tube window 67 and the tooth 114 grabs and pulls tissue into the window 67 and towards the side 70 thereof. This tissue is cut by the scissoring action between tooth 114 and the adjacent straight-edged portion 115 of the side 111 of upper window 107 and the opposed edge 70 of the housing tube window 67 as same closes. If the tooth 114 leaves a ragged edge and/or grooves the tissue in the area where cut, then with continued rotation in the direction of the arrow in FIG. 14, this ragged or grooved tissue adjacent the housing tube window 67 (as same opens again when the lower window 108 of the cutting element 33 aligns therewith) will be cut by the straight-edged portion 133 of the lower window 108 (see FIG. 10) which will effectively clean up the ragged or grooved area of tissue so as to leave a smooth-finish cut. Thus, with a single rotation of the cutting element 33 through 360 degrees within the outer housing tube 32, two types of cuts are provided, the first type of which occurs via the scissoring action between the tooth 114/straight-edged portion 115 (of the window 107) and the opposed edge 70 after the tooth 114 grabs tissue and pulls same into the window 67, and the second type of which occurs via the subsequent scissoring action between the straight-edged portion 133 (of the window 108) and the edge 70 which serves to provide a finishing or smoothing cut. Further, during rotation of the cutting element 33 in the direction indicated by the arrow in FIG. 14, the tooth 132 of the lower cutting window 108, when the housing tube window 67 opens due to its alignment with lower cutting window 108, will act in the same manner as described above with respect to tooth 114 and thus will pull tissue towards the edge 70 of the housing tube window 67. Any grooving or raggedness left in the tissue by tooth 132 will thus be cleaned up or finished by the straight-edged portion 115 of the upper window 107 when same again aligns with housing tube window 67.

Of course, it is possible to rotate the inner cutting element 33 in a direction opposite to that indicated by the arrow in FIG. 14, meaning that the tooth 116 and straight-edged portion 117 of the window 107 would rotate towards the side 71 of the housing element 32 and, in cooperation with the straight-edged portion 135 and the tooth 134 of the window 108, would cut and then smooth tissue in a similar manner as described above.

Additionally, with the window configuration of the cutting element 33 as described above, the straight-edged portions 115, 117, 133 and 135 of upper and lower windows 107 and 108 are substantially greater in their axial or longitudinal dimensions as compared to the axial or longitudinal dimensions of the teeth 114, 116, 132 and 134, the greatest longitudinal dimension of which would be at the root of the teeth. This means that, in this embodiment, there are significant lengths of straight-edged portions of the windows 107 and 108 of the cutting element 33 available to interact with the opposed straight sides or edges 70 and 71 of the outer housing tube window 67. This arrangement, coupled with the smoothing or finishing action described above, thus allows the cutting accessory according to the invention to achieve or at least approximate a straight-on-straight cutting style, while still providing the tissue-grabbing ability associated with toothed cutting edge configurations.

The cutting accessory 12 may be utilized in the forward or reverse mode, as described above, wherein the cutting element 33 rotates in either the forward direction or the reverse direction through continuous 360 degree cycles. The cutting accessory 12 may also be used in the oscillation mode, wherein the cutting element 33 is rotated a specified number of 360 degree cycles in a forward direction before reversing and rotating a specified number of 360 degree cycles in the opposite or reverse direction. In the oscillation mode, the tissue smoothing effect described above would provide a quicker clean-up of the targeted tissue at the surgical site due to the directional change in the cutting action which occurs in this mode.

It will be appreciated that the number of teeth 114, 116, 132 and 134 provided on the windows 107 and 108 of the cutting element 33 as described herein is presented only by way of example, and thus a greater or lesser number of teeth may be provided within the scope of the invention. For example, the cutting head 100 of the cutting element 33 may only be provided with one tooth 114 located at the upper window 107, and one tooth 132 located at the lower window 108 (so that the teeth 114, 132 are axially offset from one another). Alternatively, the cutting head 100 may be provided with one tooth 114 located at the upper window 107 and one tooth 134 located at the lower window 108 (so that the teeth 114, 134 are substantially vertically aligned with one another), so that there is an active tooth or tissue-grabbing ability in both the forward and reverse directions of rotation of the cutting head 100. Further, it is within the scope of the invention to provide multiple teeth at the upper and lower windows 107 and 108, which teeth can be provided in groups at the locations of the respective teeth shown in FIGS. 5 and 10. In the above-described embodiments, it is important that the tooth or teeth in one rotational direction of the cutting element 33, which can be considered the leader tooth or teeth, be axially aligned with a straight-edged portion located at the lower window 108, which straight-edged portion can be considered the follower straight-edged portion.

If desirable or necessary, suction can be provided at the surgical site by manipulating the valve 22 on handpiece 11 to draw surgical debris from the surgical site through the window 67 of the housing element 32 and the window 107 or 108 of the cutting element 32 aligned therewith, into the drive shaft suction passage 89, into the handpiece suction passage 20 and proximally through the handpiece 11 towards the suction pump.

The accessory 12 according to the invention thus achieves or at least closely approximates the straight-on-straight cutting style of conventional surgical accessories, and at the same time incorporates the desirable tissue-grabbing function of a toothed surgical accessory. This arrangement thus effectively allows the combination of two different cutting actions or styles into one tool or accessory, which is advantageous in that the surgeon need not remove the accessory 12 from the surgical site in order to achieve a different cutting style or action, and can also reduce the costs associated with purchasing multiple surgical accessories.

FIGS. 15-22 illustrate a second embodiment of the invention which will now be described. The second embodiment is generally similar to the first embodiment, the main difference being in that only a single cutting window is provided in the cutting head as compared to the dual cutting windows provided in the cutting head 100 of the prior embodiment. Components of this second embodiment which are similar or identical to components of the prior embodiment will include the same reference numbers as in the prior embodiment plus "100", and a detailed description of all components will accordingly not be provided. The surgical accessory shown in FIGS. 15-22 includes a cutting head 200 which defines a central longitudinal axis 199 and includes a tubular shaft 201 defined by a cylindrical wall 202 which encloses a hollow interior 203. The shaft 201 has a distal end 205 defining a bearing wall 206. In the illustrated embodiment, the distal end 205 is cut so as to define a window or opening 207 which opens generally sidewardly of the cutting head 200, and extends in the distal direction of the cutting element 200 up to the bearing wall 206, which bearing wall 206 closes off the distal end 205 of the drive shaft 88.

Figure 16:
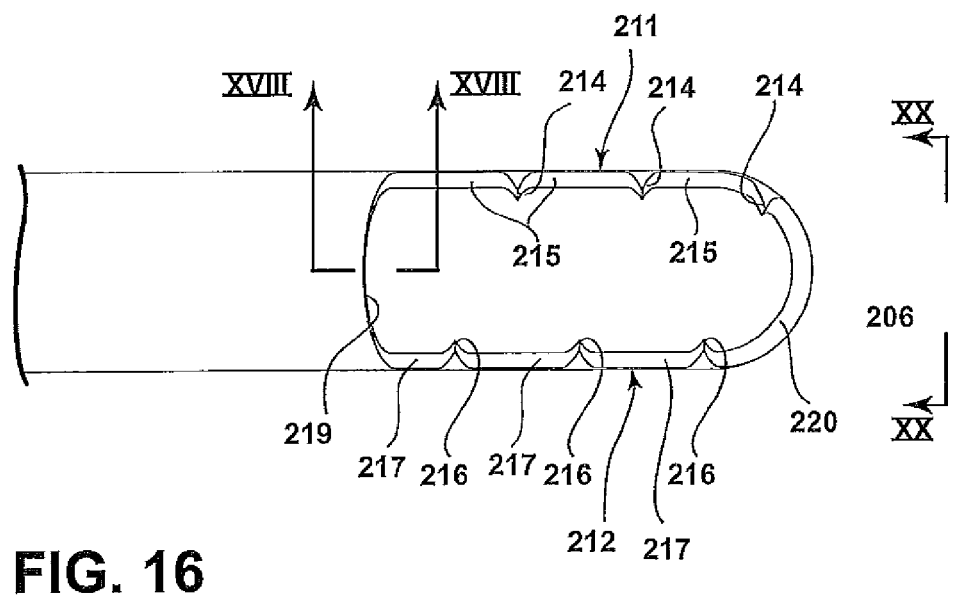
FIG. 16 is an enlarged and fragmentary top view of the cutting head of FIG. 15.
Figure 19:
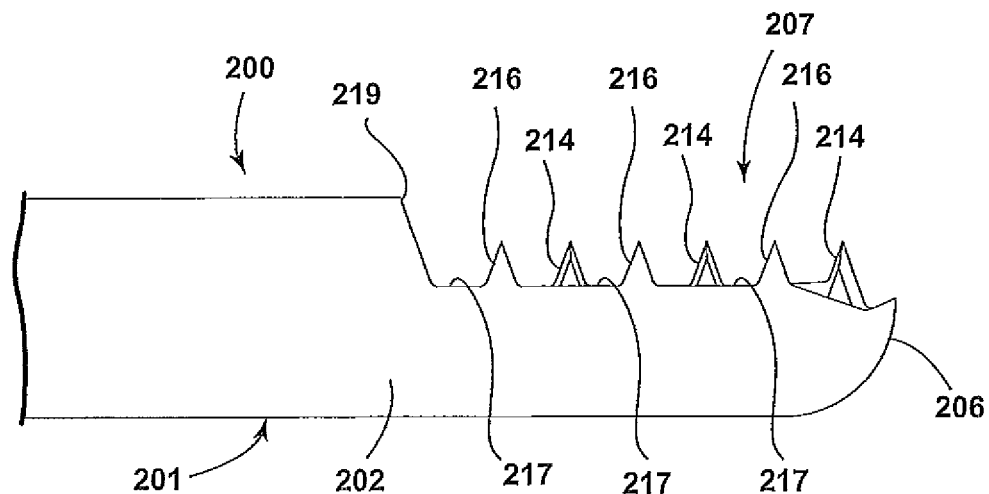
FIG. 19 is an enlarged side and fragmentary view of the cutting head of FIG. 15.
Figure 20:
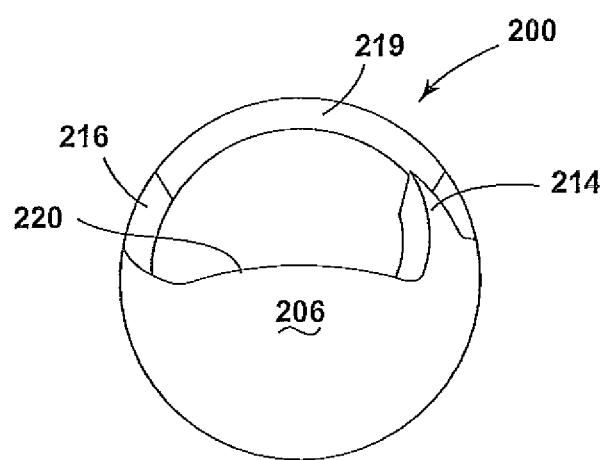
FIG. 20 is an enlarged end view of the distal end of the cutting head of FIG. 15, as seen generally along line XX-XX in FIG. 16.
Figure 21:
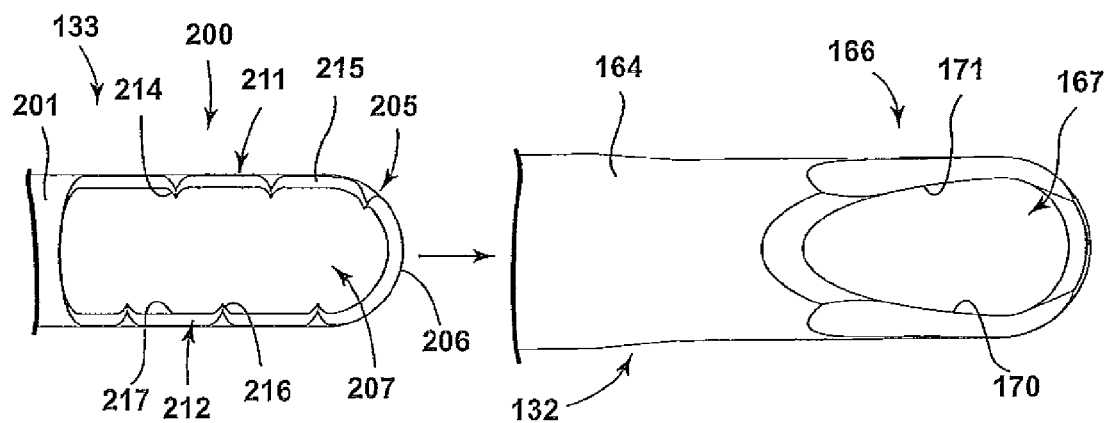
FIG. 21 is an enlarged, fragmentary and exploded top view of the of distal ends of the outer housing element and the cutting head according to the second embodiment of FIG. 15.

The cutting of the cutting head 200 results in a ring-shaped edge 209 which defines the cutting window 207. The ring-shaped edge 209 of the cutting window 207 has circumferentially-spaced, opposed and generally longitudinally-extending sides 211 and 212. The side 211 of the cutting window 207 is partially serrated or toothed, and in the illustrated embodiment includes a plurality of teeth 214. The side 211 additionally includes a plurality of substantially straight-edged portions 215 located on opposite sides of each tooth 214 (except for the most distally-located tooth 214 adjacent bearing wall 206 which has only one straight-edged portion 215 disposed at the proximal side thereof). The opposite side 212 of the window 207 is also partially serrated or toothed, and similar to the side 211 includes a plurality of teeth 216 and a plurality of substantially straight-edged portions 217 disposed on opposite sides of each tooth 216 (again, except for the most distally-located tooth 216 located adjacent bearing wall 206). The ring-shaped edge 209 of cutting window 207 additionally includes a proximal portion 219 which extends between and interconnects the proximal regions of the sides 211 and 212, and a distal portion 220 which extends between and interconnects the distal regions of the sides 211 and 212 and defines an upper edge of the bearing wall 206. As best shown in FIGS. 16 and 19, each of the teeth 214 on one side 211 of the window 207 are respectively aligned (in a direction transverse to the axis 199) with a straight-edged portion 217 on the opposite side 212 of the window 207, and each of the teeth 216 on the side 212 of the window 207 are respectively aligned with a straight-edged portions 215 on the opposite side 211 of the window 207. Further, in the illustrated embodiment, the straight-edged portions 215 and 217 are generally parallel with one another and with the axis 199.

Figure 17:
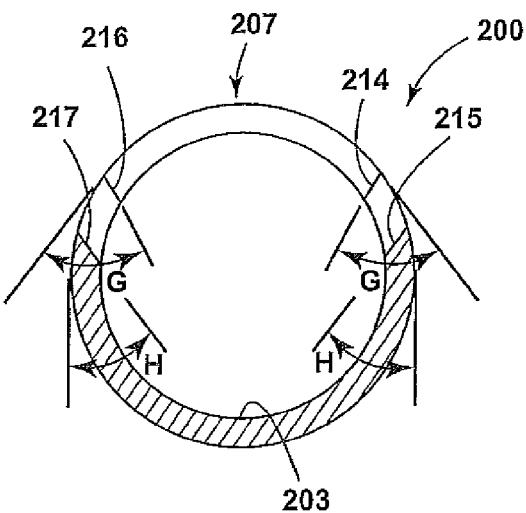
FIG. 17 is an enlarged cross-sectional view as seen generally along line XVII-XVII in FIG. 15.
Figures 18, 18A:
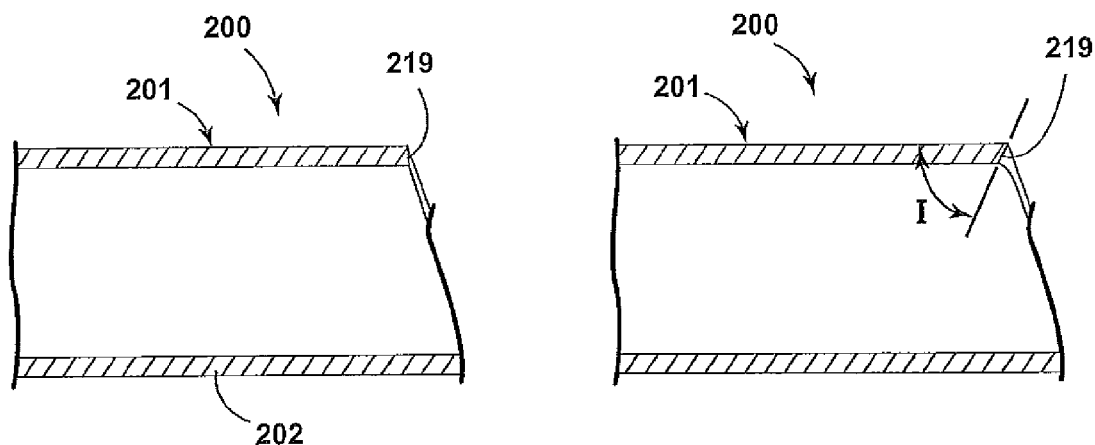
FIG. 18 is an enlarged cross-sectional and fragmentary view as seen generally along line XVIII-XVIII in FIG. 16.
FIG. 18A is an enlarged cross-sectional and fragmentary view similar to FIG. 18 of an alternative edge configuration of the proximal edge portion of the cutting window of the cutting head of FIG. 15.

As shown in FIG. 17, the cutting window 207 of cutting head 200 is provided with a geometry which maximizes the cutting abilities or characteristics of the cutting element 133. In this regard, the ring-shaped edge 209 is cut so as to provide the teeth 214 and 216 and the straight-edged portions 215 and 217 with respective included edge angles G and H which are acute. It will be appreciated that the teeth 214, 216 and/or the straight-edged portions 215, 217 may be provided with negative internal shear angles, as discussed above with respect to the first embodiment. Additionally, the internal face of the proximal edge 219 of the window 207 can be provided with a shear angle which is greater than or equal to zero degrees, as shown in FIG. 18. Alternatively, as shown in FIG. 18A, the internal faces of the edge 219 can be provided with a negative shear angle I which is less than zero degrees.

Figure 22:
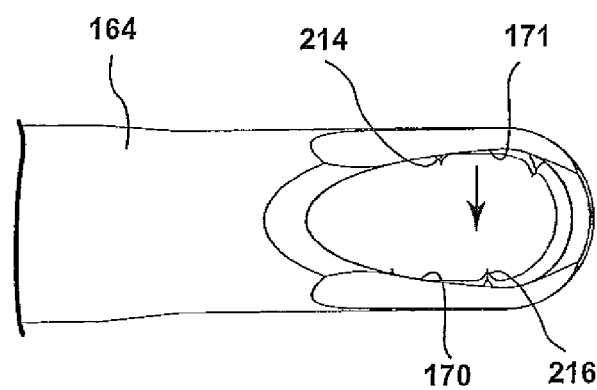
FIG. 22 is an enlarged and fragmentary top view of the cutting head of the second embodiment of FIG. 15 assembled within the distal end of the outer housing element.

FIG. 22 shows the cutting head 200 disposed within the distal end 166 of housing element 132. The cutting head 200 of this second embodiment as illustrated has a larger-sized cutting window 207 as compared to the sizes of the respective cutting windows 107 and 108 of the first embodiment. Further, the cutting head 200 includes a greater number of teeth 214 and 216 and larger-sized teeth 214 and 216 as compared to the first embodiment. The cutting head 200 is accordingly appropriate for use in situations where a more aggressive approach to tissue or bone removal is necessary and/or desirable, and as such the larger-sized window 207 allows a greater volume of tissue or bone to enter the window 207 for cutting.

The cutting head 200 may be driven in forward and reverse modes. When the cutting element 133 is rotated by the handpiece motor 15 in the direction indicated by the arrow in FIG. 22, the side 211 of the window 207 of the cutting element 133 moves towards the side 170 of the housing tube window 167 and the teeth 214 grab and pull tissue into the window 167 and towards the side 170 thereof. This tissue is cut by the scissoring action between teeth 214 and the adjacent straight-edged portions 215 of the side 211 of the window 207 and the opposed edge 170 of housing tube window 167 as same closes. In the direction of rotation opposite from the arrow shown in FIG. 22, the side 212 of the window 207 of the cutting element 133 moves towards the side 171 of the housing tube window 167 and the teeth 216 grab and pull tissue into the window 167 and towards the side 171, which causes cutting of tissue via the scissoring action between teeth 216 and the adjacent straight-edged portions 217 and the opposed edge 171 of housing tube window 167.

The cutting head 200 may also be driven in the oscillating mode which allows the surgeon to specify a number of forward cycles and a number of reverse cycles for the cutting head 200. In this regard, due to the alignment of the teeth and straight-edged portions of the cutting head 200 as described above, when the cutting head 200 is first driven in the forward mode (for example as indicated by the directional arrow in FIG. 22) for a specified number of rotational cycles, the teeth 214 may leave ragged or grooved tissue in the area(s) where cut. However, when the cutting head 200 is subsequently driven in the reverse mode (for example, in a direction opposite from the arrow in FIG. 22), any ragged or grooved tissue areas adjacent the housing tube window 167 will be cut by the straight-edged portions 217 on the opposite side 212 of the window 207 which will effectively clean up the ragged or grooved areas of tissue so as to leave a smooth-finish cut.

Additionally, with the window configuration of the cutting head 200 as described above, the straight-edged portions 215 and 217 of the window 207 are substantially greater in their axial or longitudinal dimensions as compared to the axial or longitudinal dimensions of the teeth 214 and 216, the greatest longitudinal dimension of which would be at the root or base of the teeth. As with the first embodiment, this means that there are significant lengths of straight-edged portions of the window 207 of the cutting head 200 available to interact with the opposed straight sides or edges 170 and 171 of the outer housing tube window 167, even when the cutting element 133 is simply driven in one direction of rotation. This arrangement, coupled with the smoothing action described above when the cutting head 200 is driven in an oscillating mode, thus allows the cutting accessory according to the invention to achieve or at least closely approximate a straight-on-straight cutting style, while still providing the tissue-grabbing ability associated with toothed cutting edge configurations.

It will be appreciated that the number of teeth 214 and 216 provided on the window 207 of the cutting element 133 as described herein is presented only by way of example, and thus a greater or lesser number of teeth may be provided within the scope of the invention, provided that the tooth or teeth located on one side of the window 207 of the cutting head 200 are aligned (in a direction transverse to the axis 199) with a straight-edged portion located on the opposite side of the window 207.

As with the prior embodiment, suction can be provided at the surgical site by manipulating the valve 22 on the handpiece 11 to draw surgical debris from the surgical site through the window 167 of housing element 132 and the window 207 of cutting head 200 aligned therewith, into drive shaft suction passage 89, into the handpiece suction passage 20 and proximally through the handpiece 11 towards the suction pump.

Figure 23:
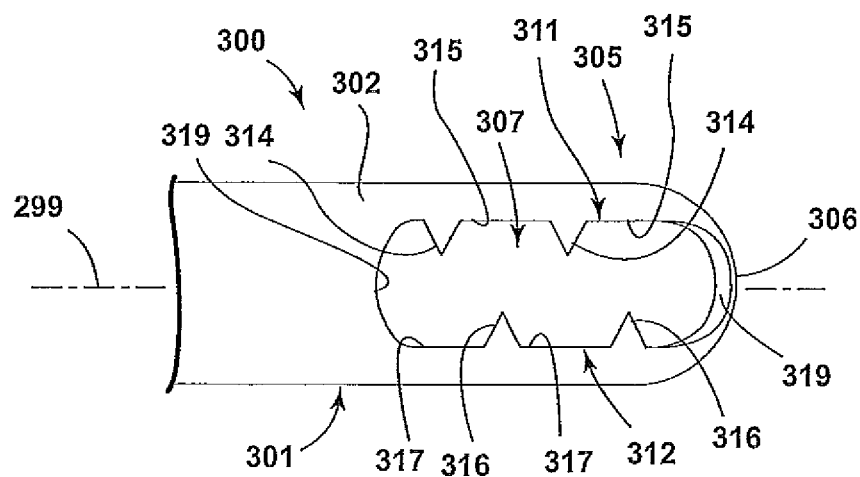
FIG. 23 is an enlarged and fragmentary top view of a third embodiment of the cutting head of the surgical accessory in isolation.
Figure 24:
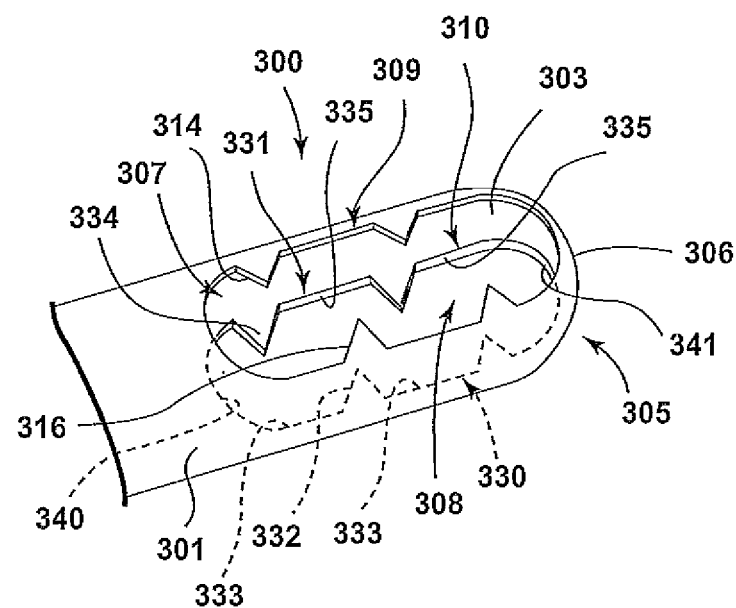
FIG. 24 is an enlarged and fragmentary perspective view of the cutting head of FIG. 23.

FIGS. 23 and 24 illustrate a third embodiment of the invention which will now be described. The third embodiment is generally similar to the first embodiment in that same includes dual cutting windows. Components of this third embodiment which are similar or identical to components of the first embodiment will include the same reference numbers as in the first embodiment plus "200", and a detailed description of all components will accordingly not be provided. The surgical accessory shown in FIGS. 23 and 24 includes a cutting head 300 which defines a central longitudinal axis 299 and includes a tubular shaft 301 defined by a cylindrical wall 302 which encloses a hollow interior 303. The shaft 301 has a distal end 305 defining a bearing wall 306 which extends transversely relative to the axis 299. In the illustrated embodiment, the distal end 305 is cut so as to define a pair of windows or openings 307 and 308 which are located generally diametrically opposite one another along opposite sides of the cutting head 300, and which open generally sidewardly thereof. The windows 307 and 308 extend in the distal direction of the cutting element 300 up to the bearing wall 306, which bearing wall 306 as in the first embodiment extends transversely between the windows 307 and 308 and defines the distal-most extent of each of the windows 307 and 308. The bearing wall 306 as such partially closes off the distal end of the drive shaft 88.

The cutting of the distal end 305 of the cutting head 300 results in a pair of ring-shaped edges 309 and 310 which respectively define the upper and lower cutting windows 307 and 308. The configuration of the edges 309 and 310 is similar to that of the first embodiment, except that additional teeth 314 are provided on one side 311 of the window 307, which teeth 314 are separated by a substantially straight-edged portion 315, and a further substantially straight-edged portion 315 is provided distally of distal-most tooth 314. Additional teeth 316 are also provided on the opposite side 312 of the window 307. The teeth 316 are separated by a substantially straight-edged portion 317, and a further substantially straight-edged portion 317 is provided between the proximal-most tooth 316 and proximal edge portion 319 of the window 307. As best shown in FIG. 23, each tooth 314 on one side 311 of the window 307 is aligned (in a direction transverse to the axis 299) with a straight-edged portion 317 on the opposite side 312 of the window 307. Likewise, each tooth 316 on the side 312 is aligned with a straight-edged portion 315 on the opposite side 311 of the window 307. Further, in the illustrated embodiment, the straight-edged portions 315 and 317 are generally parallel with one another and with the axis 299.

The lower window 308, located on the opposite side of the cutting head 300 from the window 307, on the side 330 has teeth 332 which are separated by a substantially straight-edged portion 333. The side 330 of the cutting window 308 additionally includes a substantially straight-edged portion 333 disposed directly adjacent the proximal-most tooth 332 and the proximal portion 340. The opposite side 331 of the window 308 includes teeth 334, a substantially straight-edged portion 335 disposed directly between teeth 334, and a further substantially straight-edged portion 335 located adjacent the bearing wall 306. As best shown in FIG. 23, the teeth 314 and 316 of upper cutting window 307 are respectively vertically aligned with the teeth 334 and 333 of the lower cutting window 308.

As with the prior embodiments, the cutting windows 307 and 308 of cutting head 300 are provided with geometries which maximize the cutting characteristics of the cutting head 300. Briefly, the teeth 314, 316, 332 and 334 and/or straight-edged portions 315, 317, 333 and 335 may be provided with acute included edge angles or with negative shear angles. Further, the proximal portions 319 and 340 of the windows 307 and 308 may be provided with negative shear angles.

Although particular preferred embodiments of the invention are disclosed in detail for illustrative purposes, it will be recognized that variations or modifications of the disclosed apparatus, including the rearrangement of parts, lie within the scope of the present invention.

What is claimed is:

1. A surgical cutting accessory for use with a surgical handpiece, said accessory comprising a generally tubular cutting element, a hollow interior, a proximal end and a distal end spaced therefrom, said distal end having a longitudinal axis and defining therein a cutting window in communication with said hollow interior and having circumferentially spaced-apart first and second cutting edges disposed in opposed relation with one another, said first cutting edge including a tooth and a substantially linear edge portion disposed axially adjacent said tooth, said second cutting edge including a tooth and a substantially linear edge portion disposed axially adjacent said tooth of said second cutting edge, said tooth of said first cutting edge being aligned, in a direction transverse to the axis, with said linear edge portion of said second cutting edge, said tooth of said second cutting edge being aligned, in a direction transverse to the axis, with said linear edge portion of said first cutting edge, each said linear edge portion, when viewed in cross-section in a direction transverse to the axis, defining an acute included edge angle, said tooth of said first cutting edge and said tooth of said second cutting edge each having a base and a tip spaced outwardly therefrom, each said base having a length, as measured in a direction substantially parallel with the axis, said linear edge portion of said first cutting edge and said linear edge portion of said second cutting edge each having a length, as measured in a direction substantially parallel with the axis, the length of said linear edge portion of said first cutting edge being greater than the length of said base of said tooth of said second cutting edge, and the length of said linear edge portion of said second cutting edge being greater than said length of said base of said tooth of said first cutting edge.

2. The surgical accessory of claim 1, wherein each said tooth, when viewed in cross-section transverse to the axis, defines an acute included edge angle.

3. The surgical accessory of claim 1, wherein said cutting window is a first cutting window, and said accessory further includes a generally tubular housing element having a proximal end and a distal end spaced therefrom, said distal end of said housing element defining a second cutting window therein disposed axially adjacent said first cutting window of said cutting element, said second cutting window including first and second circumferentially spaced-apart cutting edges which are generally straight in configuration, said cutting element being movably disposed within said housing element such that said first and second cutting edges of said cutting element cooperate with said first and second cutting edges of said housing element to sever tissue located within said second cutting window.

4. The surgical accessory of claim 3, wherein said cutting element is rotatably movable relative to and within said housing element in a first direction of rotation to move said first cutting edge of said first cutting window towards said first cutting edge of said second cutting window of said housing element to achieve a first tissue cut, and in a second direction of rotation opposite to the first direction of rotation to move said second cutting edge of said first cutting window towards said second cutting edge of said second cutting window of said housing element to achieve a second tissue cut during which said linear edge portion of said second cutting edge of said first cutting window acts on substantially the same area of tissue as acted upon by said tooth of said first cutting edge of said first cutting window during the first tissue cut such that the second tissue cut is smoother than the first tissue cut.

5. The surgical accessory of claim 3, wherein said distal end of said cutting element defines therein a third cutting window in communication with said hollow interior and having circumferentially spaced-apart first and second cutting edges disposed in opposed relation with one another, said first cutting edge of said third cutting window including a tooth and a substantially linear edge portion disposed axially adjacent said tooth of said third cutting window, said second cutting edge of said third cutting window including a tooth and a substantially linear edge portion disposed axially adjacent said tooth of said second cutting edge of said third cutting window, said tooth of said first cutting edge of said third cutting window being aligned, in a direction transverse to the axis, with said linear edge portion of said second cutting edge of said third cutting window, said tooth of said second cutting edge of said third cutting window being aligned, in a direction transverse to the axis, with said linear edge portion of said first cutting edge of said third cutting window, and each said linear edge portion of said third cutting edge, when viewed in cross-section in a direction transverse to the axis, defining an acute included edge angle.

6. The surgical accessory of claim 5, wherein said first and third cutting windows are located on opposite sides of said distal end of said cutting element, said first cutting edges of said first and third cutting windows of said cutting element are vertically aligned with one another and said second cutting edges of said first and third cutting windows are vertically aligned with one another, said teeth of said first cutting edges of said first and third cutting windows being generally vertically aligned with one another and said teeth of said second cutting edges of said first and third cutting windows being generally vertically aligned with one another.

7. The surgical accessory of claim 6, wherein said cutting element is rotatably movable relative to and within said housing element in a rotation cycle in a direction of rotation which moves said first cutting edge of said first cutting window of said cutting element towards and then past said first cutting edge of said second cutting window of said housing element to achieve a first tissue cut on a first area of tissue, said second cutting edge of said third cutting window in the rotation cycle moving towards and past said first cutting edge of said second cutting window of said housing element to achieve a second tissue cut during which said linear edge portion of said second cutting edge of said third cutting window acts on the first area of tissue acted on by said tooth of said first cutting edge of said first cutting window such that the second tissue cut is smoother than the first tissue cut.

8. The surgical accessory of claim 7, wherein said tooth of said first cutting edge of said first cutting window of said cutting element is axially spaced from said tooth of said second cutting edge of said third cutting window of said cutting element such that said linear edge portion of said second cutting edge of said third cutting window makes the second tissue cut on the first area of tissue.

9. The surgical accessory of claim 1, wherein said first and second cutting edges each include a plurality of teeth and a plurality of linear edge portions, said teeth and said linear edge portions on each of said first and second cutting edges being disposed in an alternating manner with one another along the respective said cutting edge, each said tooth on said first cutting edge being aligned, in a direction transverse to the axis, with one of said linear edge portions of said second cutting edge, and each said tooth on said second cutting edge being aligned, in a direction transverse to the axis, with one of said linear edge portions on said first cutting edge.

10. A surgical cutting accessory configured for being attached to and driven by a powered surgical handpiece, said surgical accessory comprising:
an outer housing assembly including a hub at a proximal end of said outer housing assembly and configured for cooperation with a coupling arrangement provided on a powered surgical handpiece, an elongate and generally tubular housing element having a proximal end connected to said hub and a distal end defining a first cutting window therein, said first cutting window having a pair of spaced-apart first and second cutting edges which are generally straight in configuration; and
a cutting element assembly including a hub at a proximal end of said cutting element assembly and configured for cooperation with a drive member of a powered surgical handpiece, and an elongate drive shaft disposed in said housing element for movement relative thereto, said drive shaft having a proximal end connected to said hub of said cutting element assembly and a distal end including a cutting head defining a longitudinal axis, said cutting head defining a second cutting window therein disposed adjacent said first cutting window of said housing element, said second cutting window having a pair of spaced-apart first and second cutting edges disposed in opposed relation with one another, said first cutting edge of said second cutting window including a tooth and a generally straight edge portion disposed axially adjacent said tooth, said second cutting edge of said second cutting window including a tooth and a generally straight edge portion disposed axially adjacent said tooth of said second cutting edge of said second cutting window, said tooth of said first cutting edge of said second cutting window being aligned, in a direction transverse to the axis, with said straight edge portion of said second cutting edge of said second cutting window, said tooth of said second cutting edge of said second cutting window being aligned, in a direction transverse to the axis, with said straight edge portion of said first cutting edge of said second cutting window, said straight edge portions each being configured for cutting hard or soft tissue, said tooth of said first cutting edge of said second cutting window and said tooth of said second cutting edge of said second cutting window each having a base and a tip spaced outwardly therefrom, each said base having a length, as measured in a direction substantially parallel with the axis, said straight edge portions each having a length, as measured in a direction substantially parallel with the axis, the length of said straight edge portion of said first cutting edge of said second cutting window being greater than the length of said base of said tooth of said second cutting edge of said second cutting window, and the length of said straight edge portion of said second cutting edge of said second cutting window being greater than said length of said base of said tooth of said first cutting edge of said second cutting window.

11. The surgical accessory of claim 10, wherein said straight edge portions, when viewed in cross-section in a direction transverse to the axis, have an acute included edge angle.

12. The surgical accessory of claim 10, wherein each said tooth, when viewed in cross-section transverse to the axis, defines an acute included edge angle.

13. The surgical accessory of claim 10, wherein said drive shaft is rotatably movable relative to and within said housing element in a first direction of rotation to move said first cutting edge of said second cutting window towards said first cutting edge of said first cutting window of said housing element to achieve a first tissue cut, and in a second direction of rotation opposite to the first direction of rotation to move said second cutting edge of said second cutting window towards said second cutting edge of said first cutting window of said housing element to achieve a second tissue cut during which said straight edge portion of said second cutting edge of said second cutting window acts on substantially the same area of tissue as acted upon by said tooth of said first cutting edge of said second cutting window during the first tissue cut such that the second tissue cut is smoother than the first tissue cut.

14. The surgical accessory of claim 10, wherein said cutting head defines therein a third cutting window having spaced-apart first and second cutting edges disposed in opposed relation with one another, said first cutting edge of said third cutting window including a tooth and a generally straight edge portion disposed axially adjacent said tooth of said third cutting window, said second cutting edge of said third cutting window including a tooth and a generally straight edge portion disposed axially adjacent said tooth of said second cutting edge of said third cutting window, said tooth of said first cutting edge of said third cutting window being aligned, in a direction transverse to the axis, with said straight edge portion of said second cutting edge of said third cutting window, said tooth of said second cutting edge of said third cutting window being aligned, in a direction transverse to the axis, with said straight edge portion of said first cutting edge of said third cutting window, and each said straight edge portion of said third cutting window, when viewed in cross-section in a direction transverse to the axis, defining an acute included edge angle.

15. The surgical accessory of claim 14, wherein said second and third cutting windows are located on opposite sides of said cutting head, said first cutting edges of said second and third cutting windows of said cutting head are vertically aligned with one another and said second cutting edges of said second and third cutting windows are vertically aligned with one another, said teeth of said first cutting edges of said second and third cutting windows being generally vertically aligned with one another and said teeth of said second cutting edges of said second and third cutting windows being generally vertically aligned with one another.

16. The surgical accessory of claim 15, wherein said drive shaft and said cutting head are rotatably movable relative to and within said housing element in a rotation cycle in a direction of rotation which moves said first cutting edge of said second cutting window of said cutting head towards and then past said first cutting edge of said first cutting window of said housing element to achieve a first tissue cut on a first area of tissue, said second cutting edge of said third cutting window in the same rotation cycle moving towards and past said first cutting edge of said first cutting window of said housing element to achieve a second tissue cut during which said straight edge portion of said second cutting edge of said third cutting window acts on the first area of tissue acted on by said tooth of said first cutting edge of said second cutting window such that the second tissue cut is smoother than the first tissue cut.

17. The surgical accessory of claim 16, wherein said tooth of said first cutting edge of said second cutting window of said cutting head is axially spaced from said tooth of said second cutting edge of said third cutting window of said cutting head such that said straight edge portion of said second cutting edge of said third cutting window makes the second tissue cut on the first area of tissue.

18. A surgical cutting accessory for use with a surgical handpiece, said accessory comprising a tubular cutting head defining a longitudinal axis and a hollow interior, said cutting head defining first and second cutting windows therein in communication with said hollow interior, said first and second cutting windows opening sidewardly of said cutting head in directions transverse to the axis, each of said first and second cutting windows having respective first and second cutting edges disposed in opposed and circumferentially spaced-apart relation with one another, said first cutting edges each including a tooth and a substantially linear edge portion disposed axially adjacent the respective said tooth, said second cutting edges each having a substantially linear edge portion, said tooth of said first cutting edge of said first cutting window being aligned, in a direction transverse to the axis, with said linear edge portion of said second cutting edge of said first cutting window, said tooth of said first cutting edge of said second cutting window being aligned, in a direction transverse to the axis, with said linear edge portion of said second cutting edge of said second cutting window, each said tooth having a base and a tip spaced outwardly therefrom and each said base having a length, defined in a direction substantially parallel with the axis, each said linear edge portion having a length, defined in a direction substantially parallel with the axis, the length of said linear edge portion of said second cutting edge of said first cutting window being greater than the length of said base of said tooth of said first cutting edge of said first cutting window, and the length of said linear edge portion of said second cutting edge of said second cutting window being greater than the length of said base of said tooth of said first cutting edge of said second cutting window.

19. The surgical accessory of claim 18, wherein said first cutting edges of said first and second cutting windows are vertically offset from one another and said second cutting edges of said first and second cutting windows are vertically offset from one another, and said teeth of said first cutting edges of said first and second cutting windows are spaced axially from one another.

20. The surgical accessory of claim 18, wherein said linear edge portions of said first and second cutting windows, when viewed in cross-section transverse to the axis, define acute included edge angles.

21. The surgical accessory of claim 18, wherein said linear edge portions are each configured to cut hard or soft tissue.

* * * * *